United States Patent [19]

Laurer

[11] Patent Number: 4,639,600

[45] Date of Patent: Jan. 27, 1987

[54] RADIATION DETECTOR

[75] Inventor: Gerard R. Laurer, Monroe, N.Y.

[73] Assignee: New York University, New York, N.Y.

[21] Appl. No.: 544,373

[22] Filed: Oct. 21, 1983

[51] Int. Cl.⁴ .............................................. G01T 1/20
[52] U.S. Cl. ............................................... 250/363 S
[58] Field of Search .......................... 250/363 S, 368

[56] References Cited

U.S. PATENT DOCUMENTS

| 4,291,228 | 9/1981 | Thompson | 250/367 |
| 4,317,037 | 2/1982 | Luzaki et al. | 250/486.1 |
| 4,395,636 | 7/1983 | Anger et al. | 250/369 |
| 4,415,808 | 11/1983 | Cusano et al. | 250/363 SB |

FOREIGN PATENT DOCUMENTS

| 56-12567 | 6/1981 | Japan | 250/363 S |
| 7812015 | 12/1978 | Netherlands | 250/368 |

Primary Examiner—Alfred E. Smith
Assistant Examiner—Richard Hanig
Attorney, Agent, or Firm—Rosen, Dainow & Jacobs

[57] ABSTRACT

The present invention provides a radiation detector arrangement wherein the detecting faces of the detecting elements are arranged at an acute angle to the plane of radiation, i.e., the plane parallel to the direction of relative movement between the radiation detector and the radiation to be detected. The remaining portions of the detector elements are shielded from receiving radiation from the source, by, for example, adjacent detecting elements or layers of high Z materials. As a consequence, the individual detector elements are sensitive to their position with respect to the radiation source, without the necessity of employing collimators. In a preferred embodiment of the invention, the individual detector elements are wedge-shaped, and are arranged in groups of four to define detectors having pyramidal recesses. In further embodiments of the invention, four detecting elements may be arranged in a back-to-back relationship, in the array, to form pyramidal detectors. Alternatively, a pair of elements may be arranged back-to-back to form detectors in an array, the detectors being wedge-shaped.

15 Claims, 20 Drawing Figures

POSITION OF S RELATIVE TO POINT O

RADIATION DETECTOR

BACKGROUND OF THE INVENTION

This invention relates to radiation detectors, and is more in particular directed to the provision of a radiation detector, for example for X-rays or gamma-rays, wherein the detector is scanned with respect to a radiation source in order to develop signals for the production of an image.

Radiation imaging detector systems such as disclosed in U.S. Pat. No. 3,011,057, Anger, have found widespread use in nuclear medicine applications as a diagnostic tool to delineate one type of tissue, e.g., cancer cells, from another by the pattern of distribution of a radioactive compound introduced into the subject's body. As currently incorporated, these systems generally employ a massive high density collimator of the multi-hole, straight-bore or focusing type to distinguish between gamma-ray photons coming from one particular direction and those coming from other directions. While these systems lend themselves to the direct formation of an image, the use of the radiation-absorbing collimator severely limits the geometrical efficiency of these devices. Thus, in nuclear medicine applications, very large amounts of radioactivity must be present to overcome the count-rate restriction of the collimator and form an image of the radioactive deposition in a reasonable time. Generally, of course, the medical benefit obtained outweighs the possible harmful effects of the radiation to the subject.

Conversely, in the field of health physics, it is often necessary to make a measurement of small amounts of a given radioactivity isotope accidentally inhaled or otherwise ingested into the body, for purposes of assessing possible long-term dose effects. For more accurate body-burden estimations, as well as dose assessment, it is necessary to know the site of deposition in addition to measuring the amount of the activity. The instrument generally employed for measuring low levels of accidentally ingested radioactivity is the whole-body counter, a shielded enclosure in which large NaI(Tl) crystals and other types of radiation detectors are used to detect and measure the gamma-ray photons being emitted from the "whole body" of the subject. These detectors, as used, have very good geometric efficiency and are thus sensitive to small amounts of radiation; however, their spatial resolution is very poor. In this case, of course, collimators cannot be used to ascertain the site of deposition because of the small amounts of radioactivity present.

In view of the disadvantage of both above types of systems—i.e., the necessity of using large amounts of radioactivity with externally collimated nuclear medicine devices and, conversely, the poor spatial resolution of uncollimated, but sensitive, devices used in health physics application, the present invention is directed to the provision of a detection system which combines the high sensitivity of a whole-body counting crystal with the spatial resolution of the detector system of U.S. Pat. No. 3,011,057.

The present invention is therefore directed to the provision of a radiation detector that overcomes the above disadvantages of prior art radiation detectors, and that simultaneously provides both high spatial resolution and high detection deficiency.

Briefly stated, the present invention provides a radiation detector arrangement wherein the detecting faces of the detecting elements are arranged at an acute angle to the plane of radiation, i.e., the plane parallel to the direction of relative movement between the radiation detector and the radiation to be detected. The remaining portions of the detector elements are shielded from receiving radiation from the source, by, for example, adjacent detecting elements or layers of high Z materials. As a consequence, the individual detector elements are sensitive to their position with respect to the radiation source, without the necessity of employing collimators.

In a preferred embodiment of the invention, the individual detector elements are wedge-shaped, and are arranged in groups of four to define detectors having pyramidal recesses. In further embodiments of the invention, four detecting elements may be arranged in a back-to-back relationship, in the array, to form pyramidal detectors. Alternatively, a pair of elements may be arranged back-to-back to form detectors in an array, the detectors being wedge-shaped. Still further, single detecting elements may be provided having pyramidal or conical recesses.

The detecting elements may be of any conventional type such as scintillation crystals, associated with corresponding photocensors, or semi-conductor radiation detectors having suitable electrodes. The invention is not limited to the type of radiation detector employed.

The outputs of the individual radiation detector elements may be processed, for example with iterative procedures, in order to develop an image of the radiation source.

In order that the invention will be more clearly understood, it will now be disclosed in greater detail with reference to the accompanying drawings, wherein.

Figure 1:
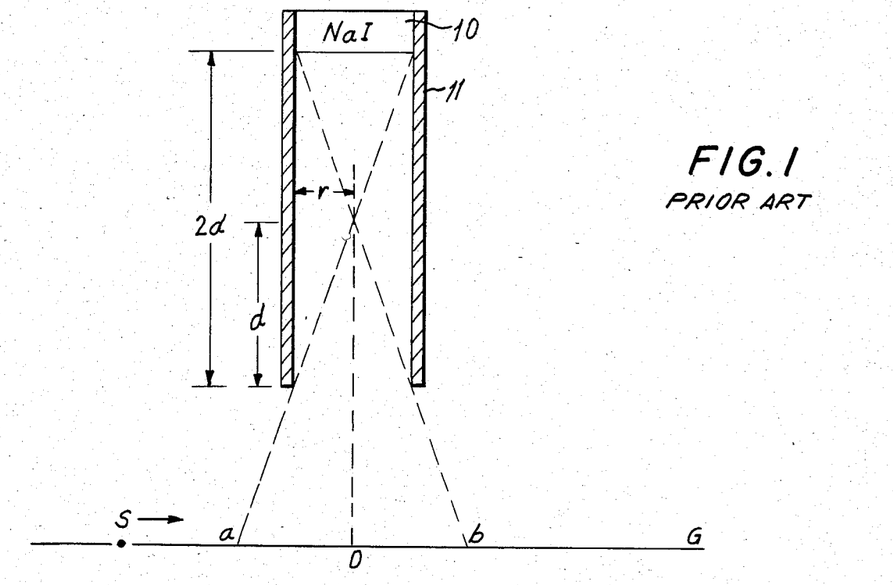
FIG. 1 is a simplified illustration of a known radiation detector element employing a collimator.
Figure 2:
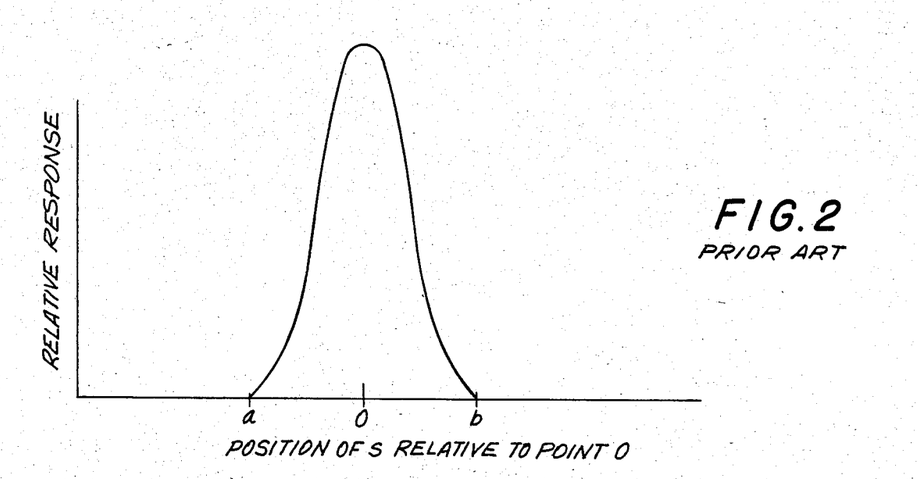
FIG. 2 is a graph of relative response of the detector of FIG. 1.

Referring now to the drawings, and more in particular to FIG. 1, therein is illustrated a cross-sectional diagrammatic representation of a typical straight-bore collimated crystal of known type, showing a NaI detector 10 placed in the conventional manner behind a high Z high density collimator 11 of a length of 2d units and internal radius r. The expected relative spatial response of the detector of FIG. 1, as a "point" source of radioactivity is moved along line G beneath the collimator is illustrated in FIG. 2. Assuming that the walls of the collimator are thick enough to absorb any photons incident thereon, the response from the detector 10 will be zero until a position a is reached, from which point it will rapidly rise to a maximum as the source passes the central line zero and then rapidly decrease to zero as it approaches the point b. The height of the response, which is directly related to the efficiency of the measurement, is a function of the distance between the detector and the source. In fact, this response is proportional to the reciprocal of the square of the distance between the source and the detector so that if the distance is halved, the response is quadrupled. The maximum response, and hence the minimum distance, is fixed by the depth 2d of the collimator.

In order to improve the geometrical efficiency of measurement of the detecting arrangement of FIG. 1, it is necessary to move the detector closer to the source by decreasing the distance 2d, i.e., making the collimator shallower. When this is done, however, the distance between the points a and b, the zero response positions on line G, become wider and wider apart and the spatial response function eventually loses its definition completely. As a consequence, with the arrangement of FIG. 1, in order to achieve high spatial resolution, it is necessary to sacrifice geometrical efficiency by use of a collimator, and vice versa, to achieve high geometrical efficiency, it is necessary to sacrifice spatial resolution.

In order to improve the spatial response of a detector without significantly reducing its counting or geometrical efficiency by the use of a high density collimator, in accordance with the invention a wedge-shaped detector element is employed.

Figure 3:
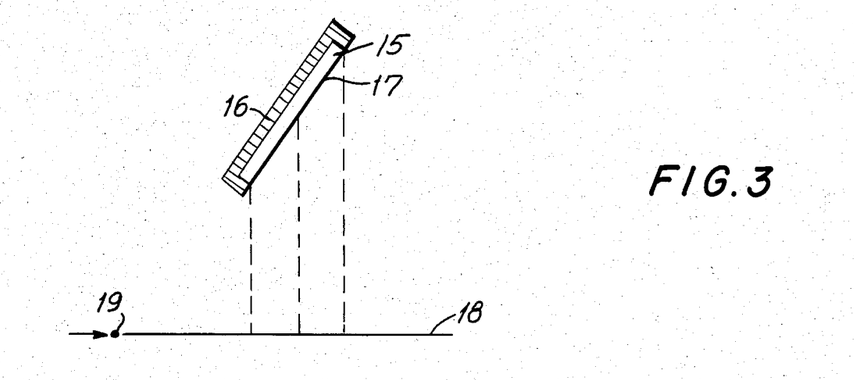
FIG. 3 is a simple illustration of the principal of the radiation detectors in accordance with the invention.

The concept of the invention may be demonstrated, for example, by providing a thin rectangular NaI(Tl) detector 15, as illustrated in FIG. 3, the detector having dimensions of 1.5 by 0.3 inches. This detector 15 is shielded by a high Z material 16 so that only one face 17 thereon is exposed. The detector 15 is mounted by any convenient means at an angle to the path 18 of a point source 19, as illustrated.

Figure 4:
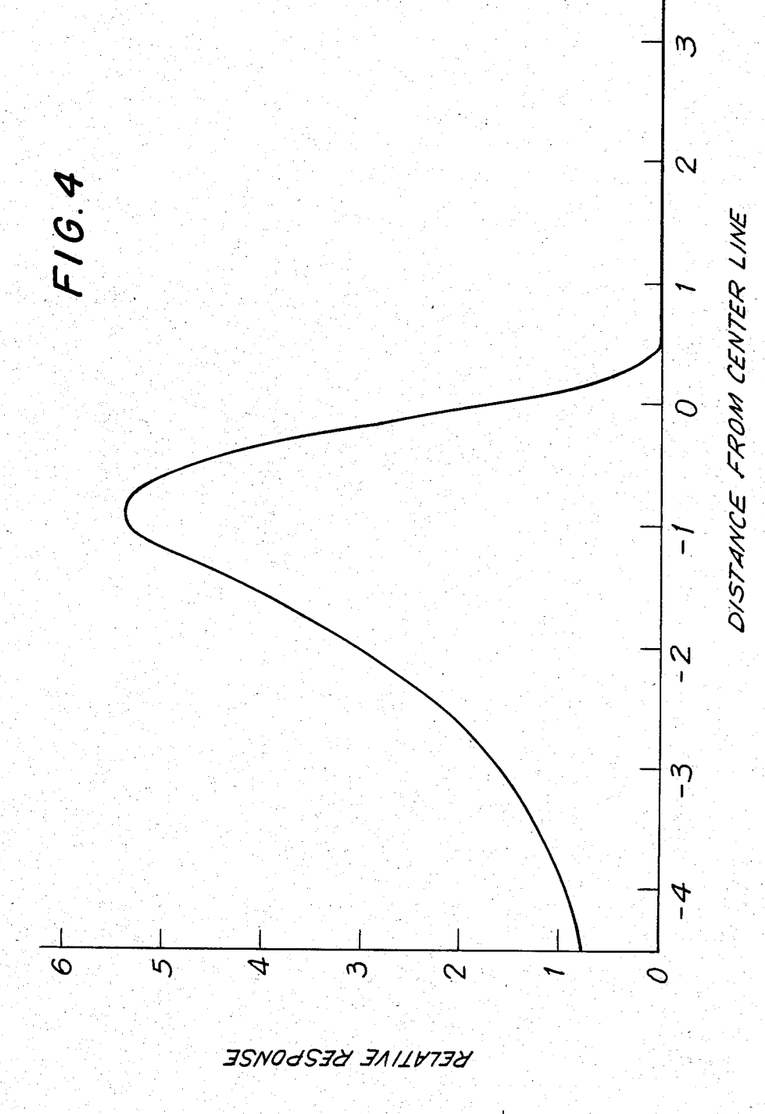
FIG. 4 is a graph of the response of the detector element of FIG. 3.

FIG. 4 is a plot of the response of the detector 15 to the "point" source 19 (<1 m diam.) of $^{241}$Am (60 keV) moved in increments of 0.1 in. beneath it. The response has a steep slope as the sensitive face comes into "view" of the source at position a, rising quickly to a maximum and then dropping more slowly. The important aspect of the response curve shown is the steep rise of the leading edge, showing that the tilted face of the wedge-shape provides a spatial response characterization comparable to a collimated detector.

Although the device used to show the above effect in the example of FIGS. 3 and 4 was a NaI(Tl) crystal, the basic objective of the detector design—i.e., high spatial resolution and high geometric detection efficiency for the simultaneous location and measurement of sources of radiation—is dependent only on the shape of the detecting element, not on its characteristics. The operating characteristics of the device in accordance with the invention are thus independent of the type of detector used and may be achieved with any of a variety of existing pulse-type radiation detectors, e.g., scintillators such as NaI and CsI employed in combination with conventional photosensitive devices; germanium (Ge) or silicon (Si) solidstate semi-conductor detectors having suitable electrodes (some or all of which may be transparent); gas-filled detectors, etc.

The thallium-activated sodium-iodide [NaI(Tl)]crystal utilized to obtain the operating characteristics of the device disclosed was an inorganic halide crystal used primarily as a gamma-ray detector. A pulse of light of approximately 400 angstroms is produced when gamma-ray photons interact and deposit energy in the crystal. The numbers of light quanta in the pulse are proportional to the energy deposited. The light output thus serves not only to indicate the detection of an event in the crystal, but also the energy of the event. The light output is converted into a voltage or current pulse proportional in height to the amount of light by means of a multiplier-phototube (PMT). Again, an output proportional to the energy of the detected event is obtainable from the other available devices mentioned above and, while it may be desirable to have proportionality in some measurement situations in conjunction with the use of the invention, it is not a necessary characteristic of the device.

Figure 5:
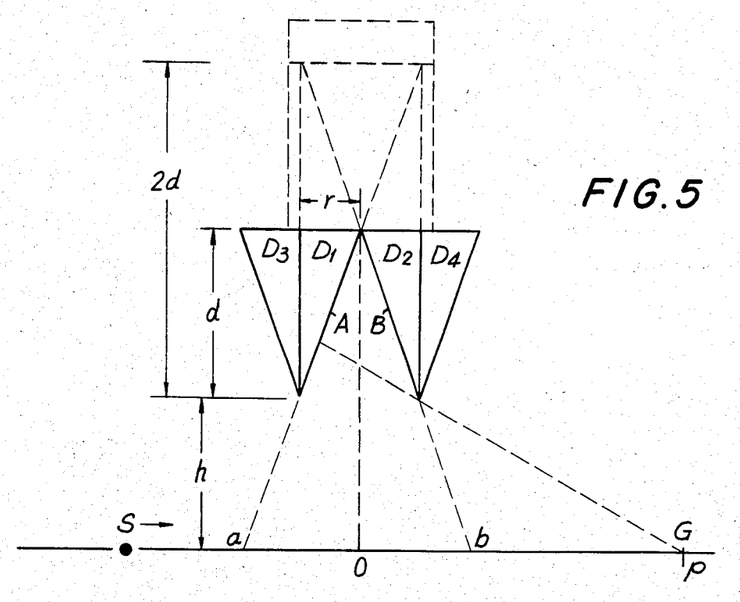
FIG. 5 is a sketch of a two dimensional radiation detector employing pairs of wedge-shaped detecting elements.

In order to illustrate in a simple manner the response obtainable from double wedge-shaped detector, a simplified, two-dimensional diagram of a pair of wedge-shaped detectors is shown in FIG. 5. A pair of wedge-shaped detectors $D_1$ and $D_2$, are shown with their active faces A and B facing each other. Further wedge-shaped detectors $D_3$ and $D_4$ are mounted back-to-back with the detectors $D_1$ and $D_2$ respectively, to define parts of adjacent detector pairs of a linear array of double wedge-shaped detectors. The corresponding position for the collimator/crystal arrangement of FIG. 1 is shown in dashed lines on FIG. 5 to illustrate the position of the wedge-shaped detector of FIG. 5 relative to the collimated detector of FIG. 1.

Figure 6:
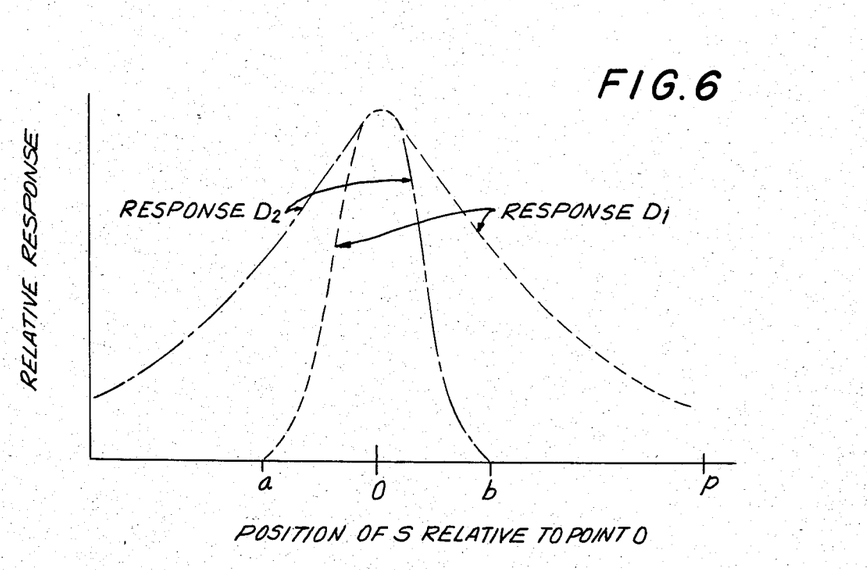
FIG. 6 is a graph of the response of the elements of FIG. 5.

Referring to FIGS. 5 and 6, the "point" source of radiation, S, again moves from right to left on line G beneath the detector elements $D_1$ and $D_2$. Assuming the photon energy is low and/or a narrow layer of high Z absorber is provided between the vertical interface of detectors $D_1$ and $D_2$ and their back-to-back counterparts $D_3$ and $D_4$ respectively, it is seen that when S is to the right of position b on line G, only surface A of detector element $D_1$ is exposed; $D_2$ will not be exposed because of the shielding effect of the detector $D_4$ to its right. Similarly, when source S is to the left of position a, the detector element $D_1$ is shielded by the detector $D_3$ to its left and only detector element $D_2$ is exposed through its active face, B. Considering now only one detector of the pair, (e.g. $D_1$) as the source passes from left to right past point b, face A will begin to be exposed and the total number of interactions will rise steeply in a short distance to a maximum at a point where the combination of the area of detector face A and the distance to the source cause the subtended solid angle to reach a maximum. The response then falls, somewhat more slowly than it rises, as the source continues to the right away from detector $D_1$ until—depending on the height h of the detector above line G—the response is reduced to zero. The response of detector $D_2$ (shown as the dot-dashed curve) is the mirror-image of the response of detector $D_1$, with reference to the point o, which is directly below the intersection of the active faces of the detectors. Hence it is seen that the fast rise portion of the response of either $D_1$ or $D_2$ is equivalent to that of a detector placed behind a collimator having a depth equal to 2d, i.e., twice the depth of the wedge-shaped element, and a radius equal to the distance r across the base of the wedge. By utilizing two wedge-shaped detector elements and mathematically combining the outputs of the two detectors, therefore, it is possible to obtain a spatial response comparable to a collimated detector and with a significant additional difference; the collimator is now effectively replaced with detectors, the result of which is a considerable increase in efficiency.

Thus far, the design of the wedge-shaped detector element has been shown in a two-dimensional form mainly for the purpose of introducing and understanding its response characteristics. It is more desirable to provide a real image, however wherein the wedge-shaped detectors are in a three-dimensional form which will allow the same spatial characteristics to be obtained relative to two axes as described above for one axis.

Figure 7:
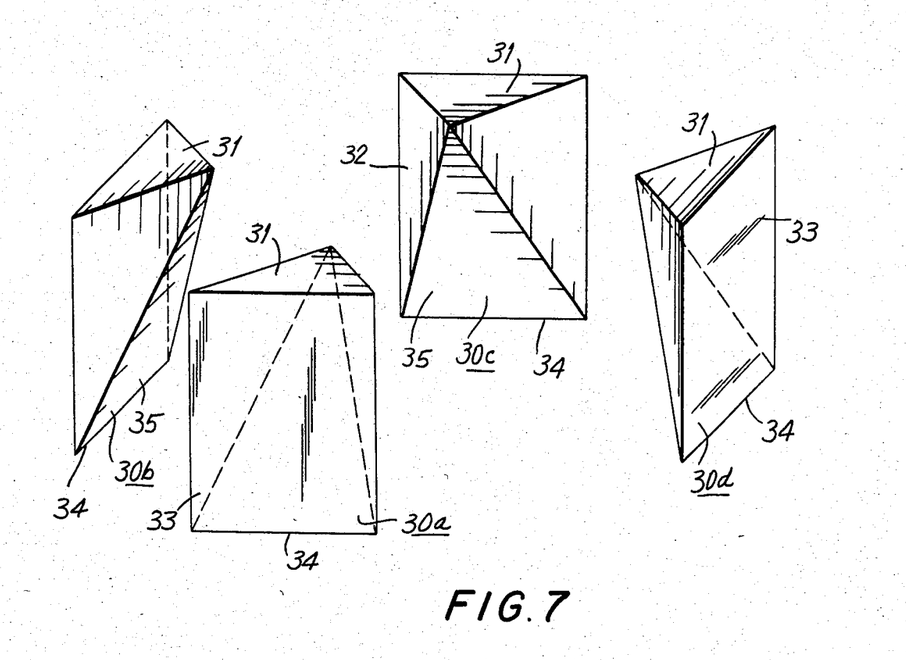
FIG. 7 is an exploded view of a four detector element detector in accordance with the invention.
Figure 8:
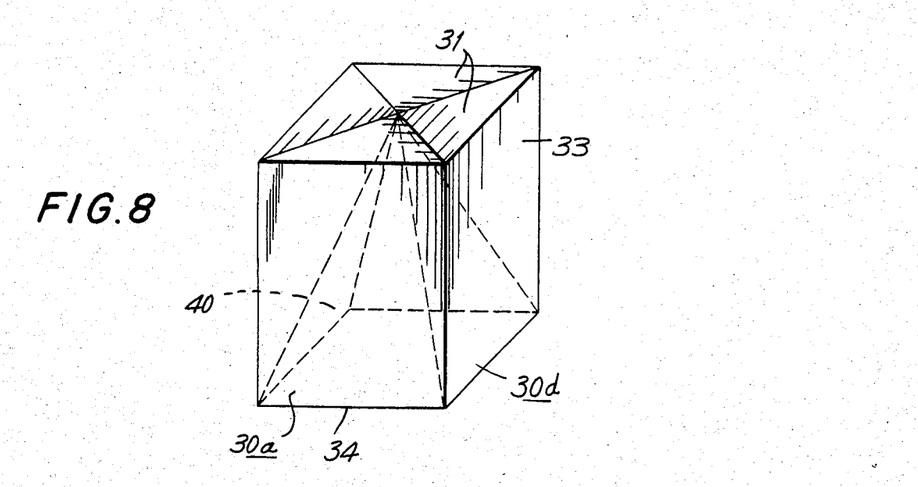
FIG. 8 is an assembled view of the detector element FIG. 7.

One three-dimensional form of the invention is illustrated in FIGS. 7 and 8, showing two aspects of the invention, i.e., the unique wedged-shape of the detector element design and the coupling of four detectors together to form a four-element detector, As illustrated in FIG. 7, four identical crystal detector elements 30a–30d are provided, the crystal elements having flat triangular tops 31 with their apices directed to a common point. The crystal elements have flat vertical sides 33 adjacent the bases of the triangular tops 31, and defining a bottom edge 34. The inner sides 35 are defined by the bottom edge 34 and the apices of the top triangular portions 31, whereby the crystal detector elements are wedged-shaped. The crystal elements are mounted to adjoin one another, as illustrated in FIG. 8, the other sides of the detector elements being shaped to adjoin one another to provide a generally rectilinear structure. As is apparent in FIG. 8, the inner surfaces 35 define a generally quadrilateral pyramid recess extending outwardly from the base thereof. In this manner, since each of the elements facing each other provides the fast-rise response shown in FIG. 6, a collimator-like response is produced for relative source motions in either direction on both the X and Y axes and thus a two-dimensional response is obtained as needed for planar imaging.

By using the four-element detectors of FIGS. 7 and 8 it is apparent that an array may be formed by joining as many of them together as needed, in a back-to-back fashion along the vertical back plane of each detector element. Arrays of this type may have suitable dimensions depending on the size of the object to be imaged.

Figure 9:
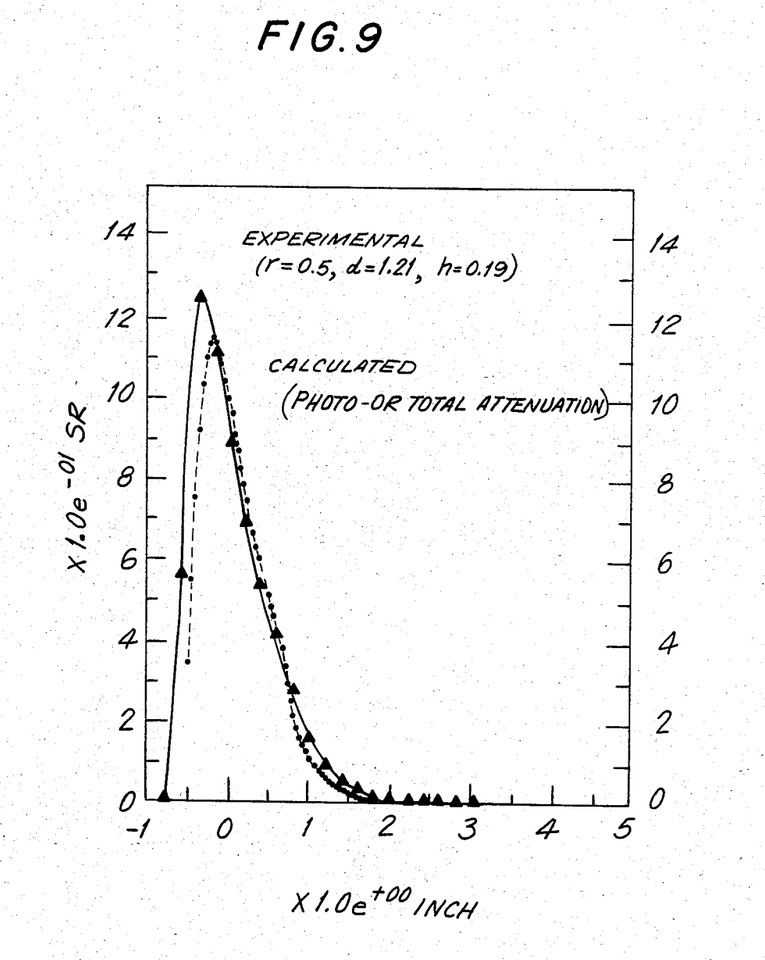
FIG. 9 is a curve showing the response of the detectors of FIGS. 7 and 8.

FIG. 9 illustrates the experimental response of a single crystal arrangement simulating the detector of FIG. 8. Since the 60 KeV photons of $^{241}$Am penetrate an NaI crystal only a fraction of a millimeter, it was possible to simulate the shielding effect of the other three wedge-shaped elements when all four are coupled together as shown by the dashed lines of FIG. 8. The response of the compound wedge-shaped element is plotted in FIG. 9 with triangular symbols. Also shown, in dotted lines for comparison, is the calculated response of the detector using as close to the same dimensions of the exposed area of the experimental crystal as possible. The source plane in this case was 0.2 in. below the detector with point o referenced to the apex of the triangle formed by the exposed portion of its shielded, tilted face. The size of the opening at the base of the shield is 1 in. square; the height of the pyramid is approximately 1.2 in. The fit between the experimental and calculated responses is very close, with the difference in the starting point of the fast-rise edge being due to the finite space between the actual crystal and its housing, not accounted for in the calculation.

At this point, it is noted that the steepness of the response and hence the resolution are affected, and may be altered, by choice of dimensions d, the depth of the detector element, and r, the width of the triangular face at the top of the element. Thus, if either d is lengthened or r is shortened, the fast rise is made steeper. In addition, however, a loss in efficiency will also occur with increasing photon energy as these dimensions change.

Figure 10:
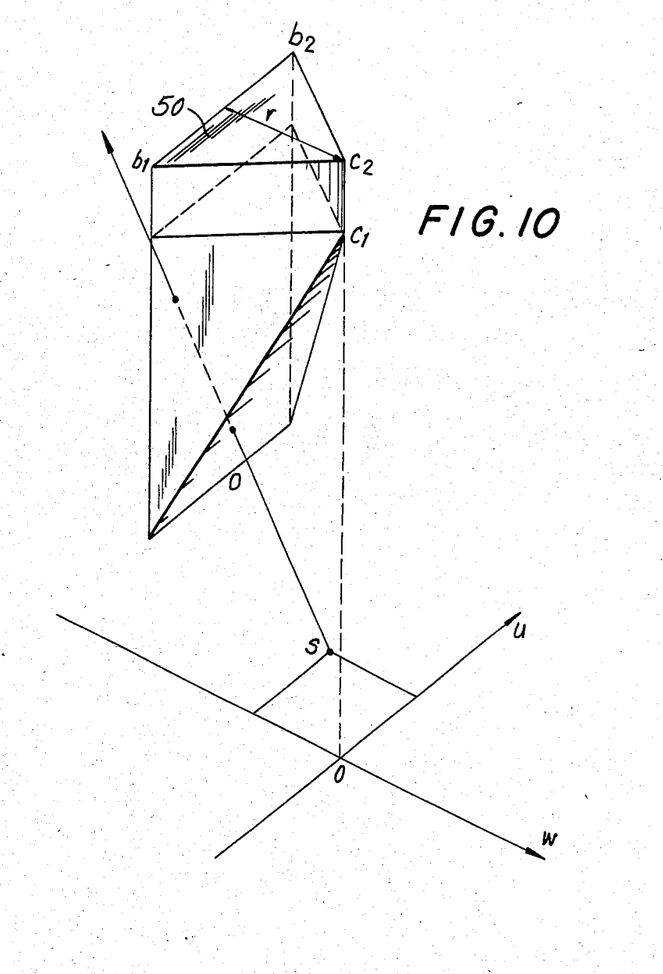
FIG. 10 is a perspective view of modified detector elements.

To compensate for efficiency loss with increasing energy, an additional wedge section 50 may be added to the top of the compound wedge-shaped element as shown in FIG. 10 with the new top surface show by lines $b_1$ to $b_2$ to $c_2$ and the added depth by the line $c_1$ to $c_2$. The added-on portion of the crystal element is hence in the shape of a triangular prism, adapted to abut the similarly shaped added on portions of the adjacent crystal elements of the detector. The added on portion may of course constitute a unitary part of the crystal element.

Figure 11:
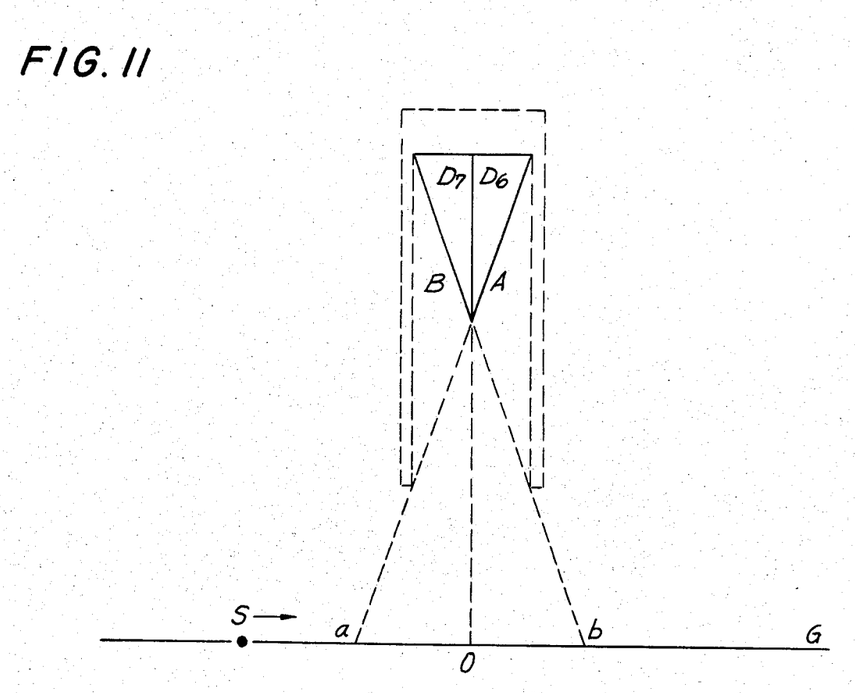
FIG. 11 is a simplified view of another embodiment of the invention, employing back-to-back detector elements to define a pyramidal detector.
Figure 12:
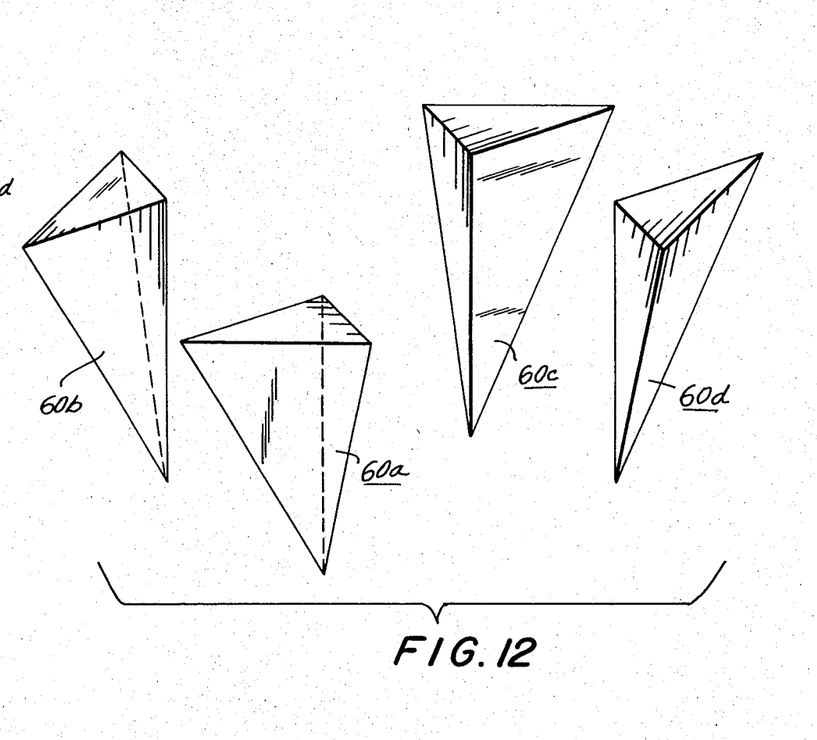
FIG. 12 is an exploded view showing the four detector elements of the embodiment of FIG. 11.
Figure 13:
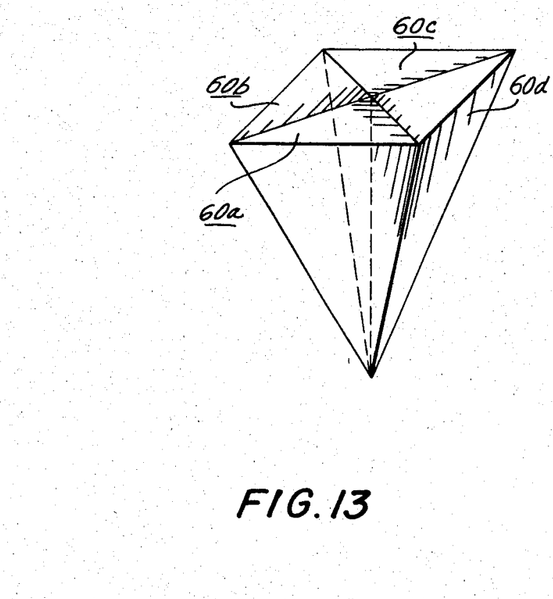
FIG. 13 is a respective view of the assembled detector employing detector elements according to FIGS. 11 and 12; employing wedge-shaped detector elements.

In accordance with the invention, the spatial response function shown in FIG. 9 may be obtained without the use of an external collimator, by inverting the wedge-shape of the detector element. This may be seen by referring to FIG. 11, showing the simplified two-dimensional representation again in which the upper portion of the zero response projection of the collimator (the dashed outline) has been replaced by wedge-shaped detector elements $D_6$ and $D_7$. In this case, while the position of the active faces and the detector elements have been reversed relative to their action in replacing the collimator, it is seen that the response will in fact be effectively the same as that shown by FIG. 5 when they are brought down to the same position above line G. As opposed to the elements shown in FIG. 5, however, these elements come to a point at the bottom, making the three-dimensional form the inverse of that shown in FIG. 8. This inverse form is shown in FIGS. 12 and 13 as formed of crystal elements 60a–60d. Since each element of the four-element detector comes to a point at the bottom, this in effect means less detector surface area will be as close to the source in the case of this wedged shape as for its inverted counterpart which has its greatest area at the bottom. This form will thus not be as efficient as the form of FIG. 8. Nevertheless, it is significantly more efficient than an externally collimated detector and, more importantly, exhibits the same high spatial resolution as the form of FIG. 8.

Figure 14:
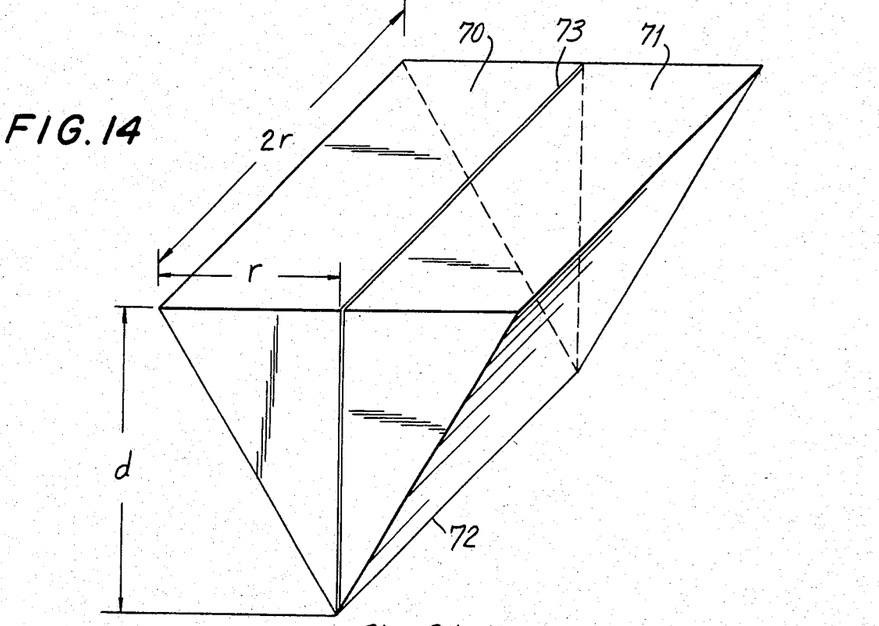
FIG. 14 is an exploded view of FIG. 5.

In a still further embodiment of the invention, the desired spatial response function may be obtained in both axial directions by extending the two-dimensional wedge-shaped detectors of FIG. 5. By dividing and optically isolating each pair of back-to-back crystals with a thin high Z absorber, as was effected with the four-element detector of FIG. 8, the same point-source response function may be obtained on both the X and Y axes by first moving the pair of detector elements along the X axes above the source, and then rotating the pair of crystals 90° and moving them along tne Y axrs. In this embodiment of the invention, as illustrated in FIG. 14, each of the back-to-back crystals 70 and 71 is in the form of a triangular prism, with a common apex 72 directed toward the radiation source, a sheet of high Z material being provided between the adjacent faces of the crystal elements. While the use of the assembly of FIG. 14 requires additional movement of the detector with respect to the source, it provides the advantage of simpler construction.

Figure 15:
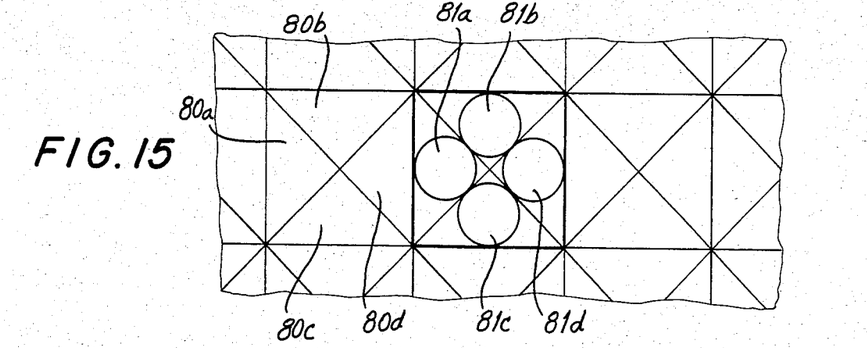
FIG. 15 is a top view of a detector array showing one arrangement of sensors.

In a preferred embodiment of the invention, as illustrated in the top view of FIG. 15, the individual detectors of an array are formed of crystal elements 80a–80d, the crystals being for example of the configuration shown in FIG. 8 or FIG. 13. A separate photosensitive detector 81a–81d is provided adjacent each of the crystal elements 80a–80d, the photosensitive elements being of a size to not be influenced by other crystal elements. (The arrangement of FIG. 15 assumes that the crystal elements are scintillation crystals.) Separate photosensitive detectors are also provided for each of the other crystal elements of the detectors of the array. In this arrangement, then, the outputs of the separate sensors are applied to a conventional calculation device, such as a computer, the outputs being separately representative of only a single one of the crystal elements.

Figure 16:
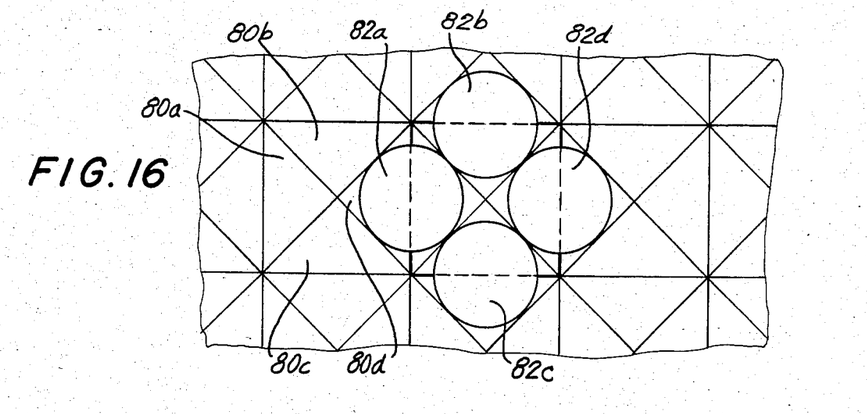
FIG. 16 is a top view of a radiation detector array showing a modification of the arrangement of the sensors.

In the modification of the invention of FIG. 15 as shown in FIG. 16, the photosensitive elements 82a–82d are positioned to sense radiation applied to separate crystal elements of one four-element detector, as well as the adjacent crystal element of the adjacent detector in back-to-back relation thereto. This arrangement reduces the required number of photosensitive elements, although rendering the acquisition of the data elements used in the image reconstruction somewhat more difficult.

In the preferred embodiments of the invention, then, the detector is comprised of an array of four-element units, separated on each side by an insert of high Z absorbing material, i.e., between adjacent vertical faces, the thickness of the high Z material depending upon the energy of the source being imaged. This parameter may easily be made flexible without engineering difficulty.

The detector elements may be of any of a variety of types—scintillation devices, solid-state devices or gaseous. Any of them can be obtained in the compound-edged shape and assembled in units of four as shown in FIG. 13. In the case of scintillation detectors in which the crystal must be coupled to a photomultiplier tube (PMT), several arrangement are possible e.g., a) one PMT on each crystal as shown in FIG. 15, or b) one phototube on each of two adjacent crystals as shown in FIG. 16. In the latter arrangement, the two adjacent crystals coupled to the single PMT may be of different materials such as NaI(Tl)/CsI(Tl) so that their outputs may be distinguished and separated by pulse-shape discrimination. This makes the electronic circuitry more complicated but allows the use of smaller crystals. Alternatively, the crystals may be coupled as a unit to an array of phototubes of larger size arranged in a light-interactionlocating, balanced-phototube array similar to the one used in the conventional camera of U.S. Pat. No. 3,011,057. This arrangement lends itself to simplification of the PMT system and the use of smaller detectors for finer resolution.

It is also possible to couple all four of the crystals in the four-crystal unit to a single PMT if a poorer resolution can be tolerated. When all four crystals are thus optically together to a single PMT in this manner the rapid rise of the spatial response function is lost. In some instances, however, e.g., where the detector can be suspended very close to a planar source and where maximum resolution is not required, this alternative is permissible.

In an alternative arrangement in accordance with the invention, the detector may be comprised of a single crystal, for example, rectilinear or cylindrical, with a conically-shaped hollow drilled or otherwise formed in the bottom of the crystal. This arrangement is somewhat simpler to form than the above discussed arrangement wherein a single PMT is coupled to four crystals of a detector, the arrangement thus having the disadvantages with respect to the arrangements, for example, of FIGS. 8 and 13, in that the resolution is diminished.

An image may be considered, mathematically, as a point-to-point or line-to-point correspondence of the projected object. For example a light projected onto a screen through a pinhole aperture is an image of the light source. The pinhole obstructs almost all of the light from the source except a narrow beam, so that a point-to-point correspondence is developed. As the hole becomes larger, however, a wider beam is allowed to pass through, the point-to-point correspondence no longer holds and, as a result, the image is blurred.

Gamma radiation and/or X-radiation is similar to light. Thus the mathematical approach to radiation imaging is to treat the data in a way that recovers the point-to-point correspondence from the response of a wide-angle detector such as the wedge-shaped element, in which the point-to-point correspondence does not exist intrinsically.

IMAGE RECONSTRUCTION

Using the detector of FIG. 8, assume that a point source of radioactivity is moving in a plane beneath the detector element. The counting rate Cp of the detector can be written as:

$$Cp = S \cdot f(u,w) \tag{1}$$

where $f(u,w)$ is referred to as the spatial response of the detector to the point source (i.e., the "point-source-response"), $u,w$ are the coordinates of the source on plane G (referenced to the detector) and S is the radioactivity of the source.

If another source is distributed in the plane G and the detector is now moved parallel to it at the same height as used to obtain the spatial response to the point source, then the counting rate C of these distributed sources becomes:

$$C(x,y) = \int_{-\infty}^{+\infty} \int_{-\infty}^{+\infty} S(u,w) \cdot f(u-x, w-y) du\, dw \tag{2}$$

where $(x,y)$ are the coordinates of the detector and $S(u,w)$ is the concentration of radioactivity at the point $(u,w)$. Since the size of the radioactive distribution is finite, the integration limits of equation (2) can be changed to reflect the limited area, e.g., $b_1<u<b_2$ and $b_3<w<b_4$. Thus, $$C(c,y) = \int_{b_1}^{b_2} \int_{b_3}^{b_4} S(u,w) \cdot f(u-x, w-y) du\, dw \quad (3)$$

In the above process of obtaining an image of a distributed source of radioactivity, in which the detector is moved parallel to the source distribution to obtain the counting rate as a function of position, and the point-source response is predetermined, it is seen that $C(x,y)$ and $f(x,y)$ in equation (3) are known and $S(x,y)$ is the image to be recovered, i.e., the actual activity distribution of the unknown source on plane G. Thus, the problem of recovering the image is equivalent to that of solving the integral equation.

There are a variety of mathematical approaches that are applicable to this problem, e.g., linear algebra, Fourier transforms, etc. For the purpose of proving the feasibility of the wedge-shaped detector in accordance with the invention, an iterative procedure was employed for the solution of the simultaneous equations that are involved when equation (3) is put into the form:

$$C(x,y) = \sum_{j=\phi}^{m} \sum_{i=\phi}^{n} [a_{ij} \cdot S(u,w) \cdot f(u-x, w-y)] \quad (4)$$

thus converting the integral equation into a set of simultaneous, linear equations by splitting the imaging area into a n x m grid and using the trapezoidal rule for numerical integration. Again, S(u,w) are the unknown variables and now there are (n x m) of them, the number depending on how the grid is divided. Since n x m equations are required, these are obtained by moving the detector in fixed steps over the distributed source area. With respect to the location of the detector, equation (4) is different for each point, so by acquiring data with one or more detectors located in different positions, as many equations as needed can be produced. Also, due to the anisotropic response of the wedge-shaped detector element, the response of each of the four coaxially oriented elements will be different from the others. Hence, four independent equations are obtained, one for each position of the four-element unit detector.

Figure 17:
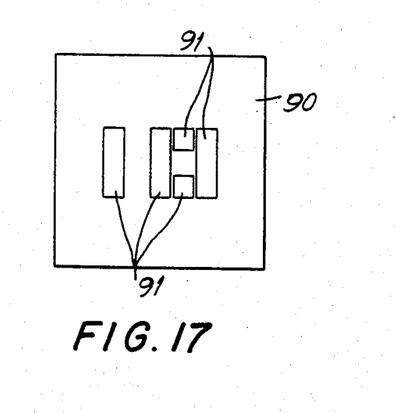
FIG. 17 is a simplified sketch of a radiation shield employed to illustrate the selectivity of the detector of the invention.

The imaging capability of the four-element detector was demonstrated with this methodology again utilizing the simulated, single wedge-shaped detector. In this case, the count-rate for all four of the coaxial elements was obtained by rotating a distributed, rectangular plated $^{241}$Am source 90, as illustrated in FIG. 17 (shielded with lead pieces 90 to yield an identifiable source configuration 91) in each of the four quadrants by counting at each of four positions in which the source was displaced by 90° for each count. Each count consisted of moving the area source beneath the detector in fixed 0.2 in. steps until an x,y counting array of 17×17 points was obtained. The point source response was obtained in the same manner by moving the $^{241}$Am "point" source in the same plane as the distributed source. In this manner, counts were obtained from both the unknown distributed source and the point source in a way which emulates the counting results that would be obtained from a 4×4 array of 1 in. square detectors of our elements each. In practice, the use of such a 4×4 array requires only 25 steps (5 in the x and 5 in the y direction, respectively) to obtain equivalent data. Since data at each point was obtained for five seconds, this means a total count time of approximately two minutes.

Figure 18:
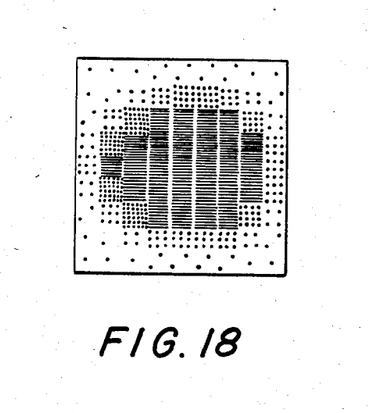
FIGS. 18, 19 and 20 are illustrations of images resulting from various iterative mathematical procedures of detector elements, employing the shield arrangement of FIG. 17.
Figure 19:
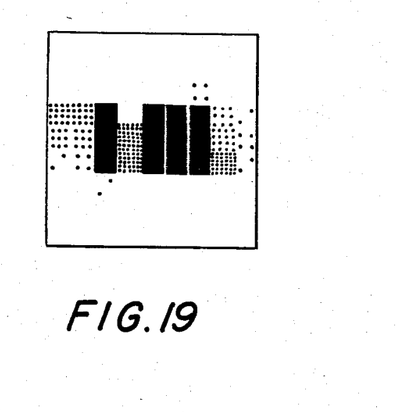
Figure 20:
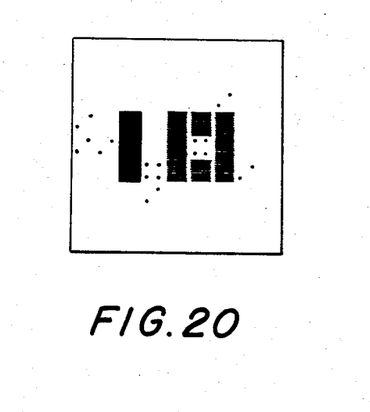

After shielding, the source area exposed was approximately a third of the total area, on which is deposited approximately a uCi of $^{241}$Am. Thus the imaging was done with approximately 300 nCi of activity (actually only about 100 nCi, since the 60 keV photons are only 35% abundant). In this example, FIG. 18 is a part of the solution of the first procedure employing the equation (4), FIG. 19 is a plot after several iterations and FIG. 20 is a plot based upon about 100 iterations of the equipment. It is seen that the resultant plot of FIG. 20 conforms very well to the shape of the Pb shielding, as provided in FIG. 17. The results of this demonstration indicate that even at this low level of activity, the equivalent of a two-minute count yielded an excellent image with a resolution of the order of 5 mm. The resolution of the camera of U.S. Pat. No. 3,011,057, Anger is of the order of 5 to 7 mm. Moreover, when compared directly with one of the commercial versions of the scintillation camera of U.S. Pat. No. 3,011,057, using the distributed $^{241}$Am source in the test, the wedge-shaped four-element detector was found to be more than 1000 times as efficient, calculated using an equivalent 12 in.×12 in. array of detectors to match the approximately 12 in. diameter of the prior art camera noted above.

While the invention has been disclosed and described with reference to a limited number or embodiments, it will be apparent that many variations and modifications may be provided within the scope of the invention. It is therefore intended in the following claims to cover each such variation and modification as falls within the true spirit and scope of the invention.

What is claimed is:

1. The method for scanning radiation from a source of radiation including scanning a radiation source in a given direction with respect to at least one radiation detector element, the detector element having a surface for receiving radiation from said source, the improvement comprising positioning at least a portion of said surface at an acute angle to said direction of relative scanning between said element and source, whereby said portion is blocked from receiving radiation from said source is predetermined regions, said step of scanning comprising scanning a source of uncollimated radiation in said given direction while maintaining said surface at said angle.

2. The radiation scanning method of claim 1 wherein said step of scanning comprises scanning a radiation detector element that is wedge-shaped and has a planar detecting surface in a plane at an acute angle to the direction of relative scanning between said element and source.

3. The radiation scanning method of claim 2 wherein said step of scanning comprises scanning a detector element having a planar back side normal to said direction of relative scanning and a planar top surface parallel to said direction of relative scanning.

4. In a radiation detector assembly wherein a radiation source is adapted to be scanned by at least one radiation detector element, the detector element having surface for receiving radiation from said source, the improvement wherein at least a portion of said surface is at an acute angle to the direction of relative scanning between said element and source, whereby said portion is blocked from receiving radiation from said source in predetermined regions, said surface being position to receive uncollimated radiation from said source, said detector element being pyramidal and having an apex toward the path of relative movement of said source.

5. In a radiation detector assembly wherein a radiation source is adapted to be scanned by at least one radiation detector element, the detector element having a surface for receiving radiation from said source, the improvement wherein at least a portion of said surface is at an acute angle to the direction of relative scanning between said element and source, whereby said portion is blocked from receiving radiation from said source in predetermined regions, said surface being positioned to receive uncollimated radiation from said source, said surface comprising a pyramidal recess extending into said detector element.

6. In a radiation detector assembly wherein a radiation source is adapted to be scanned by at least one radiation detector element, the detector element having a surface for receiving radiation from said source, the improvement wherein at least a portion of said surface is at an acute angle to the direction of relative scanning between said element and source, whereby said portion is blocked from receiving radiation from said source in predetermined regions, said surface being positioned to receive uncollimated radiation from said source, said surface comprising a conical recess extending into said detector element.

7. In a radiation detector assembly wherein a radiation source is adapted to be scanning by at least one radiation detector element, the detector element having a surface for receiving radiation from said source, the improvement wherein at least a portion of said surface is at an acute angle to the direction of relative scanning between said element and source, whereby said portion is blocked from receiving radiation from said source in predetermined regions, said surface being positioned to receive uncollimated radiation from said source, said radiation detector having at least four of said radiation detector elements adjoining one another with the radiation receiving surfaces thereof defining a pyramidal recess in said detector.

8. In a radiation detector assembly wherein a radiation source is adapted to be scanned by at least one radiation detector element, the detector element having a surface for receiving radiation from said source, the improvement wherein at least a portion of said surface is at an acute angle to the direction of relative scanning between said element and source, whereby said portion is blocked from receiving radiation from said source in predetermined regions, said surface being positioned to receive uncollimated radiation from said source, said radiation detector comprising at least four of said radiation detector elements joined together to form a detector, the radiation receiving surfaces of said elements defining a pyramid having an apex directed toward said source.

9. In a generally planar radiation detecting array comprised of a plurality of radiation detectors; the improvement wherein each of said radiation detectors is comprised of a plurality of detecting elements, the detecting elements of each detector being arranged with planar radiation receiving surfaces in different planes at an acute angle to the plane of the array, said detector elements being wedge-shaped and having facing radiation receiving surfaces defining a pyramidal recess in the respective detector.

10. In a generally planar radiation detecting array comprised of a plurality of radiation detectors; the improvement wherein each of said radiation detectors is comprised of a plurality of detecting elements, the detecting elements of each detector being arranged with planar radiation receiving surfaces in different planes at an acute angle to the plane of the array, the elements of each said detector having radiation receiving surfaces directed oppositely to defining a pyramid.

11. The radiation detector array of claim 10 wherein each said detector is comprised of four wedge-shaped radiation detecting elements, each said detector abutting at least one other detector, and separate sensors for each radiation detecting element.

12. The radiation detecting array of claim 10 wherein each detector is comprised of four wedge-shaped detector elements, the detector elements of each detector abutting detector elements of at least one adjacent detector, and a plurality of sensors optically coupled to the detecting elements, with each sensor being arranged to sense radiation received by at least one radiation detecting element.

13. The radiation detector array of claim 12 wherein the adjacent detectors of the array have different radiation receiving characteristics.

14. The radiation detecting array of claim 10 wherein each said sensor is positioned to sense radiation received by a single radiation detecting element.

15. The radiation detecting array of claim 12 wherein each said sensor is arranged to sense radiation received by abutting radiation detecting elements of adjacent detectors.

* * * * *